(12) United States Patent
Wu et al.

(10) Patent No.: US 6,945,285 B2
(45) Date of Patent: Sep. 20, 2005

(54) APPARATUS AND METHOD FOR COLLECTING FLUID FRACTIONS

(75) Inventors: Jhy-Wen Wu, Hsin-Chu (TW);
Nan-Kuang Yao, Tao-Yuan (TW);
Yuan-Fong Kao, Hsin-Chu (TW);
Tim-Kuei Shia, Taichung (TW);
Shaw-Hwa Parng, Kaohsiung (TW)

(73) Assignee: Industrial Technology Research Institute, Chu-Tung (TW)

( * ) Notice: Subject to any disclaimer, the term of this patent is extended or adjusted under 35 U.S.C. 154(b) by 55 days.

(21) Appl. No.: 10/437,073

(22) Filed: May 14, 2003

(65) Prior Publication Data

US 2004/0226627 A1 Nov. 18, 2004

(51) Int. Cl.[7] .................................................. B67C 3/00
(52) U.S. Cl. ........................ 141/31; 141/130; 141/236; 141/324
(58) Field of Search ........................ 141/31, 130, 234, 141/236, 324

(56) References Cited

U.S. PATENT DOCUMENTS

| | | | | | |
|---|---|---|---|---|---|
| 1,325,991 | A | * | 12/1919 | King ............................ | 141/59 |
| 2,884,021 | A | * | 4/1959 | Ginsburg ..................... | 141/35 |
| 4,454,773 | A | * | 6/1984 | Brunner et al. .......... | 73/863.31 |
| 5,872,010 | A | * | 2/1999 | Karger et al. ............... | 436/173 |
| 6,450,218 | B1 | | 9/2002 | Andersson | |
| 6,602,472 | B1 | * | 8/2003 | Zimmermann et al. ..... | 422/100 |
| 2002/0094533 | A1 | * | 7/2002 | Hess et al. ..................... | 435/6 |
| 2003/0175165 | A1 | * | 9/2003 | Liu ............................. | 422/100 |

* cited by examiner

*Primary Examiner*—J. Casimer Jacyna
(74) *Attorney, Agent, or Firm*—Birch Stewart Kolasch & Birch LLP

(57) ABSTRACT

An apparatus and a method for collecting fluid fractions. The present apparatus includes an inlet, a channel, a plurality of collectors, and an outlet. The inlet communicates with the collectors and the outlet through the channel. The collectors are disposed between the inlet and the outlet. The method for collecting the fluid fractions comprises two steps. First step, injecting the fluid in to the inlet for guiding the fluid to the outlet along the channel, wherein the fluid fills the collectors one by one due to the capillary attraction when passing through the collectors, and flows to the outlet after the collectors having been filled. Second step, injecting pressurized gas into the channel to drain the fluid fractions from fill the collectors respectively to a plurality of corresponding containers.

14 Claims, 4 Drawing Sheets

APPARATUS AND METHOD FOR COLLECTING FLUID FRACTIONS

BACKGROUND OF THE INVENTION

1. Field of the Invention

The present invention relates to an apparatus and a method for collecting fluid fractions, and more particularly, to collect the fluid fractions by capillary attraction.

2. Description of the Prior Art

Numerous fluid fraction collectors are known, for example through U.S. Pat. No. 6,450,218, which is an appendix to this specification. FIG. 1 is a schematical perspective view of the apparatus of U.S. Pat. No. 6,450,218. The prior apparatus provides a collector 2 for dispensing liquid from a liquid source (not shown) to receptacles 4 that are positioned on a rotatable turntable 6. The turntable 6 is connected to a fraction collector casing 8 via a support arm 10 such that the turntable 6 is rotatably mounted at one end of the support arm 10. The support arm 10 at its other end being rotatably mounted to the fraction collector casing 8. Thereby, it is possible to align any position of the turntable 6 under a dispensing tube 14, which is positioned on a holding arm 12 to dispense the liquid into one of receptacles 4 placed anywhere on the turntable 6.

The prior apparatus combines the features of a resting outlet tube, short attached tubing length and small bench space required for the turntable collector. Thus, the fraction collector 2 can be provided with different size receptacles, including provided with the receptacles different sizes on the same turntable 6. Since the receptacle 4 moves, rather than the dispensing tube does, the risk of missing drops is reduced. As the dispensing tube is at rest with respect to the receptacles 4, it can be positioned very near the outlet of any liquid feeding device, such as the outlet of a liquid chromatography column, thereby providing for the possibly shortest attached tubing.

Even though the collector 2 of the prior apparatus provides many advantages, it is not good enough. The collector 2 is very expensive and not easily moved when it is necessary to move the collector 2 to another plate. The collector 2 may cost thousands dollars or more. When it is necessary to collect a special fluid, e.g. a poison fluid, that should exist in a special space, e.g. a vacuum space, it is difficult to move the collector 2 to the vacuum space for collecting the poison fluid. The collector 2 may need and electronic apparatus for controlling the fluid to drop into the receptacles 4 respectively during a period of time, or controlling the position between the receptacles 4 and the dispensing tube 14.

Therefore, it is an intention to provide an improved apparatus for collecting fluid fractions, which can overcome the drawbacks of the prior pparatus.

SUMMARY OF THE INVENTION

An objective of the present invention is to provide an inexpensive apparatus for collecting fluid. The apparatus of the present invention uses PMMA plates and capillary tube tubes. Therefore, the cost for manufacturing the cost for manufacturing the present apparatus is inexpensive.

It is another object of the present invention to provide a convenient method for collecting fluid fractions. Because the present apparatus is easily operated, movable and small size, it can be easily moved to any place.

It is a further objective of the present invention to provide a method and an apparatus for collecting the unmixed and constant quantity fluid fractions during a period of time.

The present invention provides an apparatus and a method for collecting the fluid fractions without an electronic apparatus for controlling the position, the quantity and the reaction time of the fluid. The present apparatus includes an inlet, a channel, an outlet and a plurality of collectors. The inlet connects to the collectors and the outlet channel. The collectors are disposed between the inlet and the outlet. The present method comprises two steps for collecting fluid fractions. First step, injecting the fluid into the inlet for guiding it to the outlet along the channel and being collected by the collectors one by one due to the capillary attraction when passing through the collectors, and flows to the outlet after the collectors have been filled. Second step, receiving the fluid after the collecting of the fluid becomes overabundant. The receiving step further comprises injecting pressurized gas into the channel so that the fluid fractions, that have been collected by the collectors respectively, are forced to drain respectively from the collectors to a plurality of respective containers.

All these advantageous features as well as others that are obvious from the following detailed description of preferred embodiments of the invention are obtained.

DESCRIPTION OF THE PREFERRED EMBODIMENT

The preferred embodiments of the present invention that provide an apparatus and a method for collecting fluid fractions will now be described in greater detail below. Nonetheless, it should be recognized that the present invention can be practiced in a wide range of other embodiments besides those explicitly described, and the scope of the present invention is expressly not limited except as specified in the accompanying claims.

Figure 1:
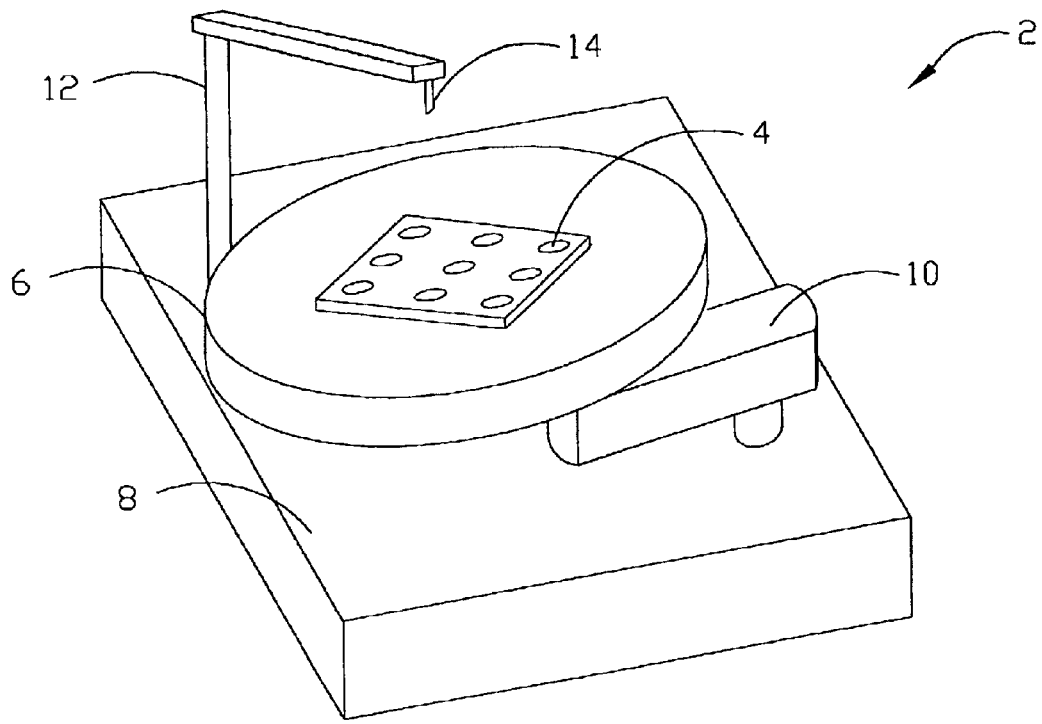
FIG. 1 is a schematical perspective view of a prior apparatus for collecting fluid fractions.
Figure 2A:
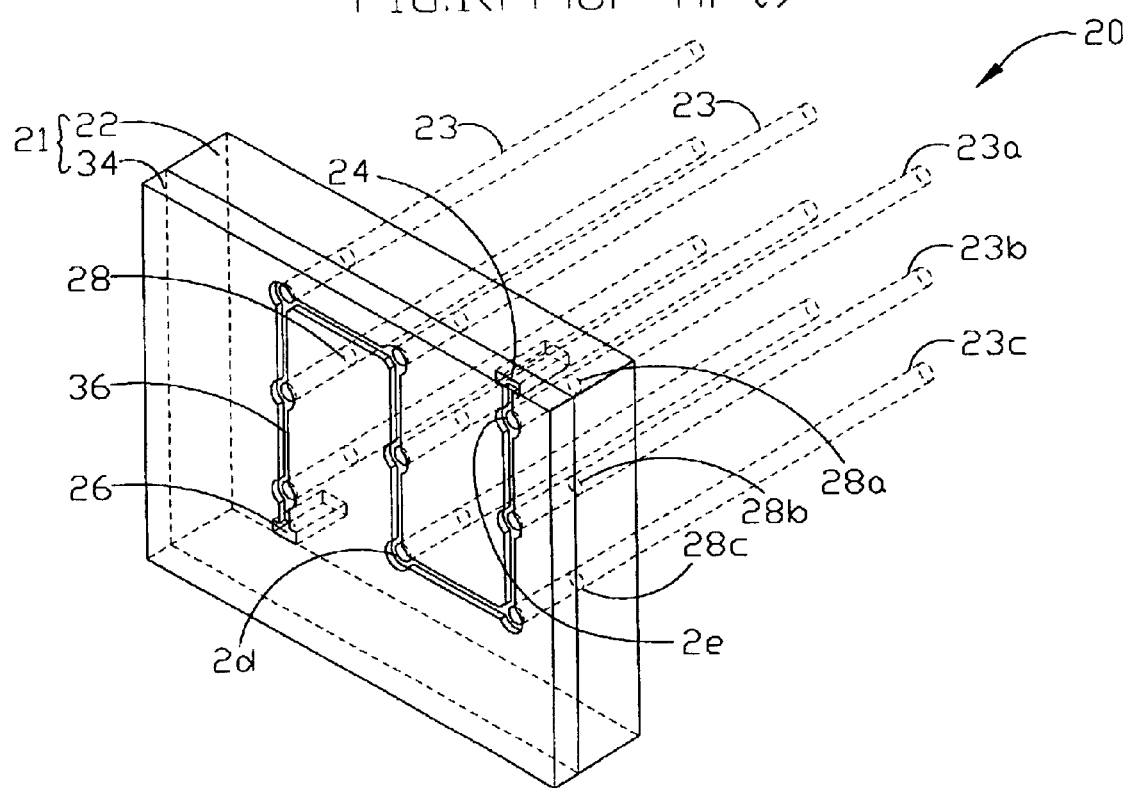
FIG. 2a is a schematical perspective view of a first embodiment of the present invention.

As shown in FIG. 2a, a schematical perspective perspective view of a first embodiment of the present inventionis provided. An apparatus 20 for collecting fluid fraction comprises a channel system 21 and a plurality of collectors 23. The channel system 21 includes an inlet 24, an outlet 26, a plate 22, a plurality of holes 28 through the plate 22, a channel 36, and a plate 34 that is adhered unto the plate 22. The holes 28 include holes 28a, 28b and 28c. The channel includes a first end and a second end (not shown), and the inlet 24 is positioned on the first end and the outlet 26 is positioned on the second end. The inlet 24 connects to the holes 28 and the outlet 26 with the channel 36. The holes 28 are positioned between the inlet 24 and the outlet 26, and connect to each other in a series-connected manner. The channel 36 is a bent-shaped channel, for example like a word of 'S'. Each collector 23 is connected with one of the holes 28, and is constructed with a plurality of capillary tubes 231. As shown in FIG. 2d, seven capillary tubes 231a constitute the collector 23.

Figure 2B:
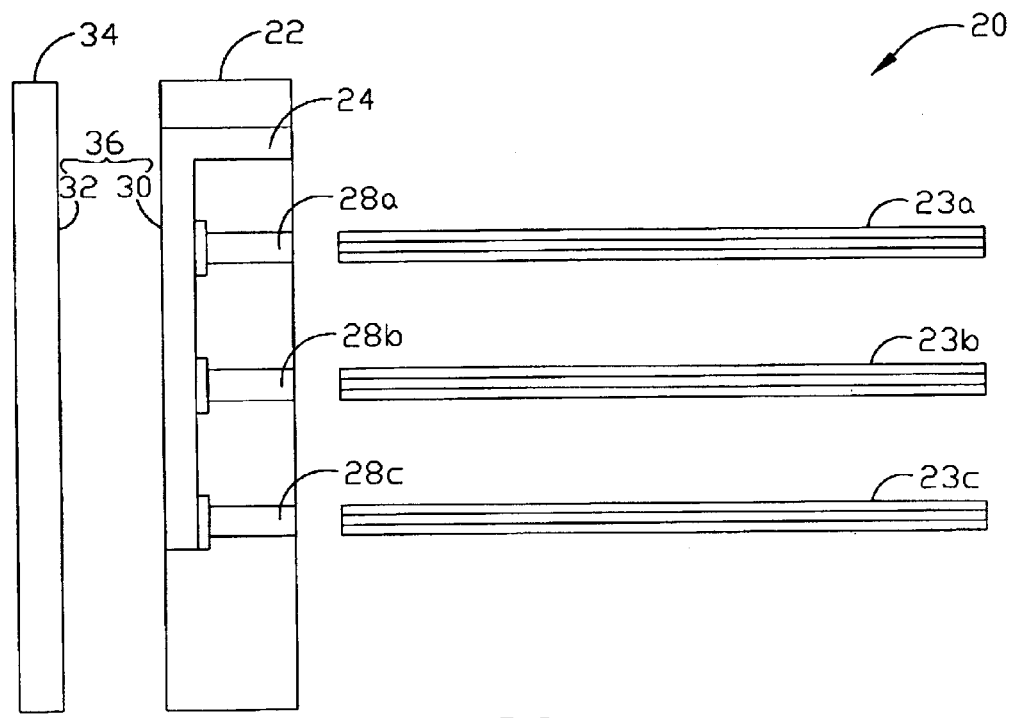
FIG. 2b is an exploded side view of the first embodiment of the present invention.

FIG. 2b shows an exploded side view of the first embodiment of the present invention. A surface 32 of the plate 34 is adhered to the plate 22 to form the channel 36 with a groove 30 on the plate 22. The channel 36 connects with the inlet 24, the outlet 26 and the holes 28 including the hole 28a, the hole 28b and the hole 28c, for guiding fluid from the inlet 24 to the outlet 26 along the channel 36. The material of the plate 34 and the plate 22 are the same. The plate 22 may be a non-hydrophilic plate as like a PMMA (PolyMethyl MethAcrylate) plate so that the plate 34 may be a PMMA plate or a non-hydrophilic membrane.The channel 36 is a non-hydrophilic channel as like a PMMA channel but the material of the capillary tubes 231 is hydrophilic.

The depth and the width of channel 36 are about 1 mm respectively. The capillary tube 231 of the collectors 23 has a caliber that is about 0.65 mm so as to cause the capillary attraction.

The method for collecting fluid fraction of the present invention comprises two steps. First step, injecting the fluid into the inlet 24 to guide the fluid to the collectors 23 for collecting the fluid due to the capillary attraction and the outlet 26 along the channel 36. The collectors 23 collect the fluid fractions one by one due to the capillary attraction, when the fluid passing through the collectors 23.

Figure 2C:
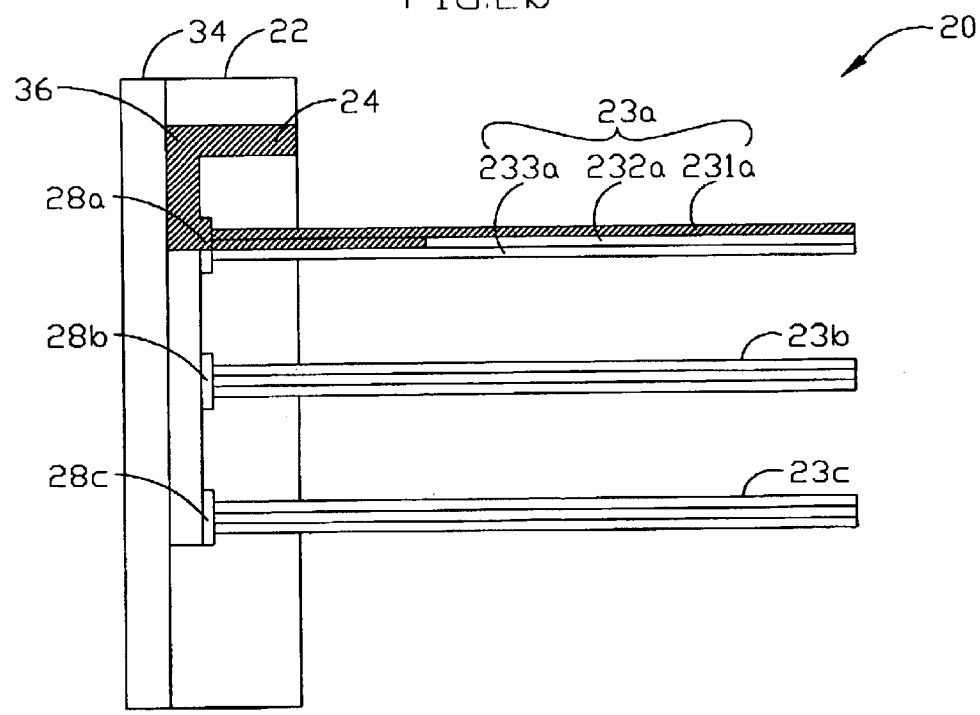
FIG. 2c is a side view of the first embodiment of the present invention, showing that a fluid fraction fills a collector due to capillary attraction.
Figures 2D, 2E:
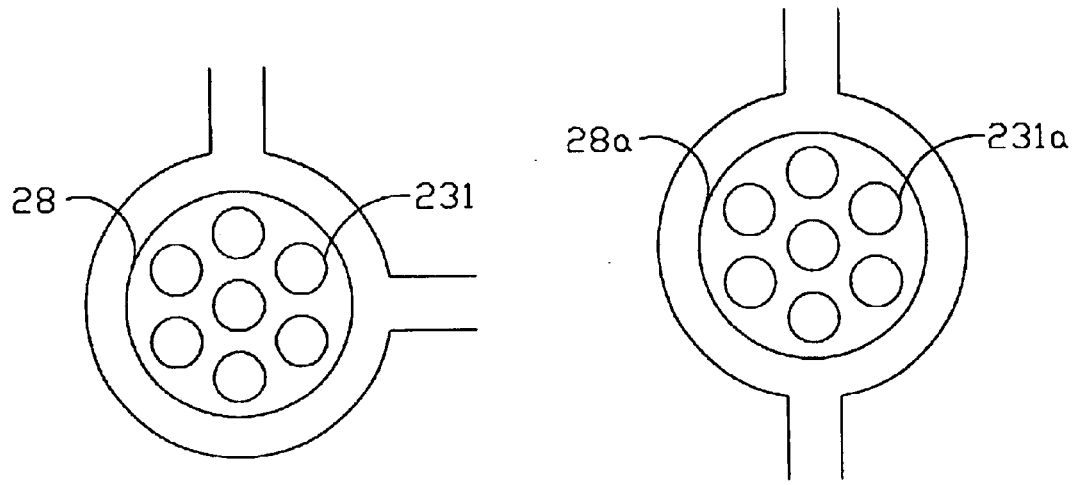
FIG. 2d is a partial enlarged top view of the collector of the first embodiment.
FIG. 2e is a partial amplifying view of the first embodiment.

As shown in FIG. 2c, a side view of the first embodiment of the present invention is provided. The fluid flowing from the inlet 24 along the channel 36 will flow into the hole 28a at first, and then fill the capillary tube 231a, which the fluid contacts first, of the collector 23a, due to the capillary attraction. Until all capillary tubes 231a of the collector 23a collect the fluid fractions. Then, the fluid will be guided to the hole 28b, as shown in the FIG. 2c. The fluid is guided from the inlet 24 to the hole 28a, and then is guided to the hole 28b and fills the collector 23b along the channel 36 after the collector 23a being filled with the fluid. After the collector 23b collect the fluid fraction, the fluid is guided to the hole 28c and fills the collector 23c. Similarly, the fluid is guided to other holes 28 and fills the collectors 23 that are respectively positioned in the respective holes 28 one by one, due to the capillary attraction. The fluid is guided to the outlet 26 along the channel 36 after all collectors 23 have collected the fluid fractions.

Second step is receiving the fluid after the collecting of the fluid becomes overabundant. The receiving step is injecting pressurized gas into the channel 36 so that the fluid fractions, that fill the collectors 23 respectively, are forced to be drain respectively from the collectors 23 to a plurality of respective containers that are not shown.

The reason for the collectors 23 capable of collecting the fluid fractions, and the fluid being not able to flow to the next collector 23, until the previous collector 23 being filled, is due to the capillary attraction. When the fluid flowing along the channel 36 to fill the collectors 23, the fluid that was collected by one of the collectors 23, and that flows along the channel 36 will not mix to each other due to the resistance of the fluid fraction that fills the collector 23. That is to say, the fluid fractions that are collected by different collectors 23 do not mix to each other.

The present invention provides an apparatus and a method of collecting fluid fractions according to a period of reaction time for producing the fluid and the capacity of the fluid.

The flowing velocity of the fluid in the channel 36 and in a collector 23 can be calculated. For example, assuming the time for filling a collector 23 with the fluid is 30 seconds, and the time for guiding the fluid from a collector 23 to the next collector 23 is 10 seconds. If several fractions of fluid produced by the reaction from 1 second to 30 seconds, 61 seconds to 90 seconds, and 121 seconds to 150 seconds are needed, injecting the fluid produced by the reaction into the inlet 24 as the reaction beginning. After five collectors 23 are filled with fluid fractions, stoping injecting the fluid into the inlet 24. Draining the fluid fractions filled the collector 23a, the collector 23c and the fifth collector 23 out, because those collectors 23 are filled with the fluid fractions produced by the reaction from 1 second to 30 seconds, 61 seconds to 90 seconds, and 121 seconds to 150 seconds, respectively.

The capacity of each collector 23 being constructed from the capillary tubes 231 can be calculated for the required capacities of fluid fractions.

Figure 3A:
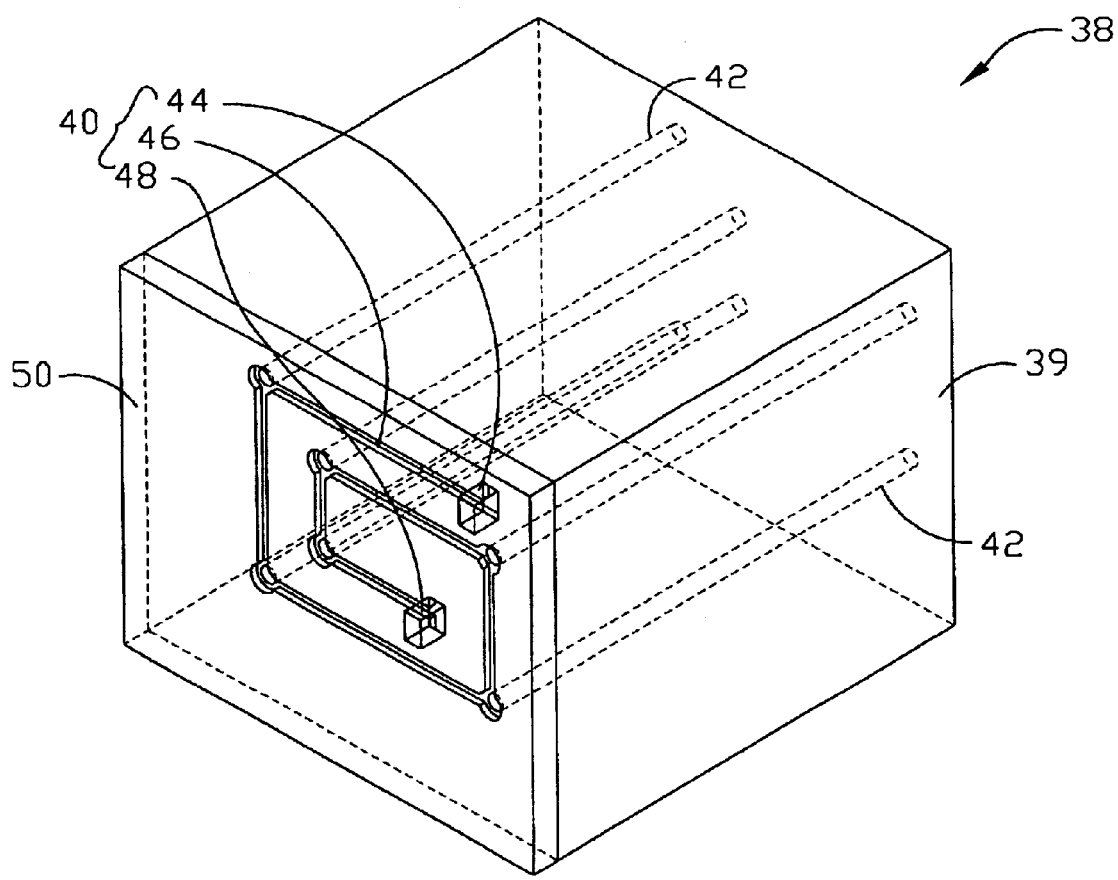
FIG. 3a is a schematical perspective view of a second embodiment of the present invention.

A schematically perspective view of a second embodiment is shown in FIG. 3a. The apparatus 38, that is formed in a lump 39, for collecting fluid fractions of the present invention, includes a channel system 40 and a plurality of collectors 42. The channel system 40 includes an inlet 44 on a first end of a channel 46 and an outlet 48 on the other end of the channel 46. The collectors 42 are connected with the channel 46 between the inlet 44 and the outlet 48, and are formed inside the lump 39 by etching or drilling through the lump 39.

The lump 39 is a non-hydrophilic lump as like a PMMA lump. The channel 46 is a non-hydrophilic channel and is formed between the lump 39 and a plate 50 that is a non-hydrophilic plate as like a PMMA plate or a non-hydrophilic membrane. The channel 46 is a curved channel as a word—G. The plate 50 is a non-hydrophilic plate, as like a PMMA plate or a membrane. The plate 50 includes two holes, connecting with the inlet 44 and the outlet 48 respectively, for injecting and draining the fluid. The collectors 42 being formed through the non-hydrophilic lump 39 are hydrophilic-cannular channels that are formed by depositing a hydrophilic layer on the innersurface of each collecotr 42 for attracting the micfluidics by capillary attraction.

Figure 3B:
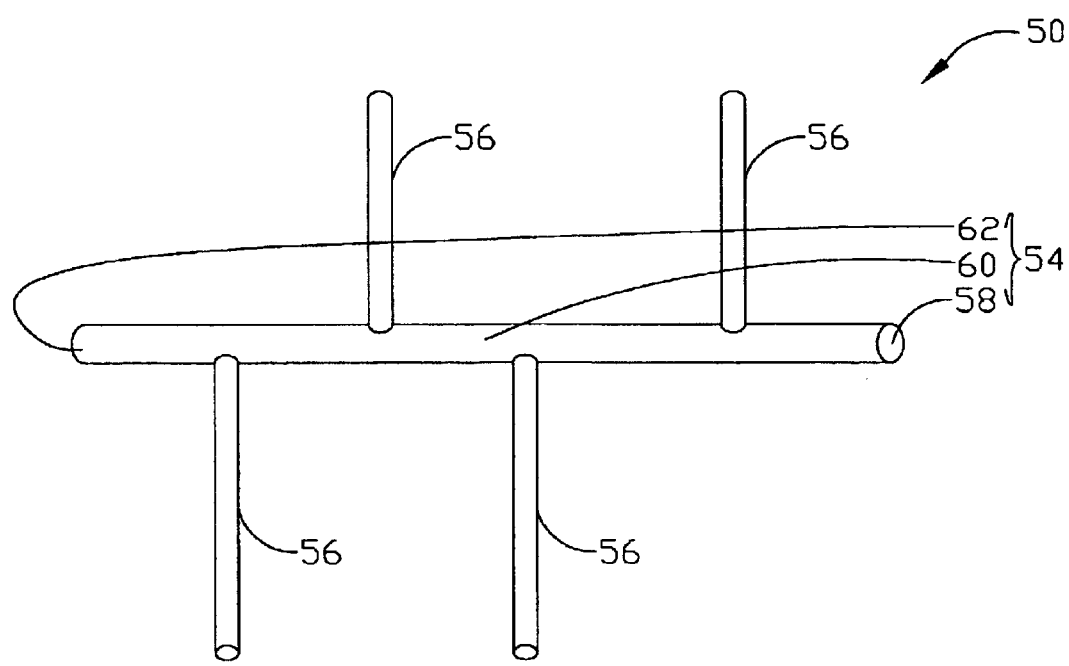
FIG. 3b is a schematical partially perspective view of the third embodiment of the present invention.

A schematical partially perspective view of a third embodiment is shown in FIG. 3b. The apparatus 50 for collecting fluid fractions of the present invention includes a channel system 54 and a plurality of collectors 56. The channel system 54 includes an inlet 58, a channel 60 and an outlet 62. The collectors 56 connect with the channel 60 between the inlet 58 and the outlet 62.

The channel 60 is a straight cannular tube, and is a non-hydrophilic tube as like a PMMA tube. The collectors 56 are hydrophilic cannular tubes for collecting the micfluidics fractions due to capillary attraction. Each collector 56 may be constructed with a plurality of capillary tubes for collecting fluid fractions from the channel 60 due to capillary attraction.

The method for collecting the fluid fractions of the first, second and the third embodiment is the same. Injecting the fluid into the inlet 24, 44 and 58, respectively, to guide the fluid to flow toward the outlet 26, 48 and 62, respectively. After fill the collectors 23, 42 and 50, respectively, injecting pressurized gas into the channel 26, 46 and 60 to drain the fluid out.

In each embodiment of the present invention, the channels are non-hydrophilic for guiding the fluid from the inlet to the outlet, and the collectors are hydrophilic for collecting the fluid fractions due to capillary attraction.

Each channel of the present invention is a non-hydrophilic channel formed in a plate, as shown in FIG. 2a, or a lump, as shown in FIG. 3a, or a non-hydrophilic cannular tube, as shown in FIG. 3b. The channel 46 in the lump 39, as shown in FIG. 3a includes a depth and a width with about 1 mm in depth and about 1 mm in width, for example.

Each collector in the present invention, can be a collector with several capillary tubes, a hydrophilic cannular tube or a hydrophilic tunnel formed in a lump. The caliber of each capillary tube, each hydrophil cannular tube and each tunnel is about 0.65 mm in the first embodiment.

Figure 4:
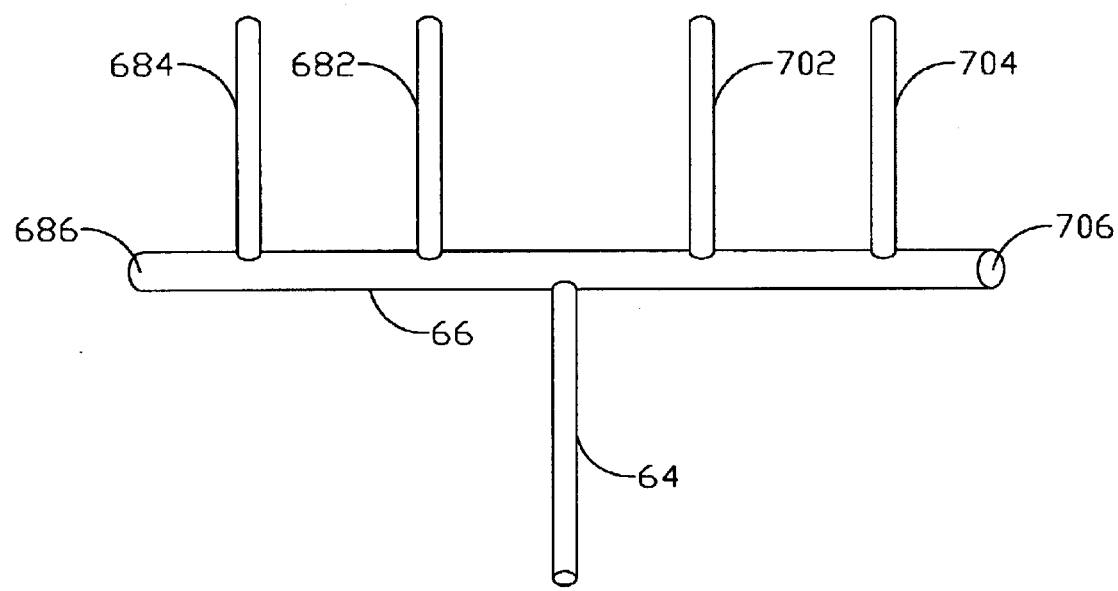
FIG. 4 is a schematical partially perspective view of the fourth embodiment of the present invention.

The fourth embodiment, as shown in FIG. 4, comprises a second outlet 706 that is disposed on a first end of a channel 66. An outlet 686 is disposed on a second end of the channel 66 and an inlet 64 is positioned between the outlet 686 and the second outlet 706. A plurality of second collectors 702 and 704 connect with the channel 66, and are disposed between the inlet 64 and the second outlet 706. The inlet 64 connects with a plurality of collectors 682 and 684 and the outlet 686 by the channel 66. The collectors 682 and 684 are disposed between the outlet 686 and the inlet 64. The inlet 64 also connects with the second collectors 702 and 704 and the outlet 706 so that the fluid, that is injected into the inlet 64, flows to the collector 682 and the second collector 702 at the same time. Until the collector 682 and the second collector 702 are filled with the fluid fractions, the fluid flows to the following collectors—the collector 684 and the second collector 704, and then flows to the outlet 686 and the second outlet 706.

The present invention provides a convenient method and an inexpensive apparatus for collecting fluid fractions with constant quantity and un-mixed with each other. The present apparatus collects the fluid fractions without an electronic apparatus for controlling the position, the quantity and the period of the reaction time for producing the fluid. The reaction time and quantity of the fluid could be calculated. The cost for manufacturing the present apparatus is lower than the apparatus in the prior art, because the cost, of the present invention, of a PMMA plate (or a PMMA lump) and the capillary tubes are inexpensive. Besides, the collecting method of the present invention is more convenient than the collecting method in the prior art, because the apparatus of the present invention is simple constructed movable and small size.

The described above is only to demonstrate and illustrate the preferred embodiments of the present invention, not to limit the scope of the present invention to what described detailed herein; and any equivalent variations and modifications of the present invention should be within the scope of the claims hereafter.

What is claimed is:

1. An apparatus for collecting fluid fractions, comprising:
    a channel system including an inlet, an outlet and a channel; and
    a plurality of collectors connecting with said channel respectively and being disposed between said inlet and said outlet, each of said collectors being constructed with a plurality of capillary tubes.

2. The apparatus for collecting fluid fractions according to claim 1, wherein said channel is a non-hydrophilic channel and said collectors are hydrophilic collectors.

3. The apparatus for collecting fluid fractions according to claim 1, wherein said channel is formed between a surface of a lump and a surface of a plate.

4. The apparatus for collecting fluid fractions according to claim 3, wherein said plate is a membrane.

5. The apparatus for collecting fluid fractions according to claim 1, wherein said channel is about 1 mm in depth and about 1 mm in width.

6. The apparatus for collecting fluid fractions according to claim 1, wherein the caliber of each said capillary tube is about 0.65 mm.

7. The apparatus for collecting fluid fractions according to claim 3, wherein said collectors are formed in said lump.

8. The apparatus for collecting fluid fractions according to claim 7, wherein said collectors are hydrophilic cannular tunnels that are formed by depositing hydrophilic material on inner surfaces of a plurality of cannular tunnels of said lump.

9. The apparatus for collecting fluid fractions according to claim 1, wherein said channel comprises a first end and a second end.

10. The apparatus for collecting fluid fractions according to claim 9, wherein said channel is a straight channel.

11. The apparatus for collecting fluid fractions according to claim 9, wherein said channel is a bent-shaped channel.

12. The apparatus for collecting fluid fractions according to claim 9, wherein said inlet is disposed on said first end, and said outlet is disposed on said second end.

13. The apparatus for collecting fluid fractions according to claim 9, further comprising a second outlet that is disposed on said first end of said channel, wherein said outlet is disposed on said second end and said inlet is disposed between said outlet and said second outlet.

14. The apparatus for collecting fluid fractions according to claim 13, further comprising a plurality of second collectors connect with said channel, and are disposed between said inlet and said second outlet.

* * * * *